United States Patent [19]

Russell

[11] Patent Number: 5,112,866
[45] Date of Patent: May 12, 1992

[54] ETHANESULFONAMIDE DERIVATIVES

[75] Inventor: Ronald K. Russell, Titusville, N.J.

[73] Assignee: Ortho Pharmaceutical Corporation, Raritan, N.J.

[21] Appl. No.: 391,797

[22] Filed: Aug. 14, 1989

Related U.S. Application Data

[63] Continuation-in-part of Ser. No. 240,976, Sep. 6, 1988, Pat. No. 4,874,771.

[51] Int. Cl.⁵ .................. A61K 31/185; A61K 31/445; C07C 211/29; C07D 211/18
[52] U.S. Cl. .................... 514/576; 514/213; 514/237.5; 514/299; 514/331; 514/408; 540/484; 544/159; 544/398; 544/399; 544/400; 546/232; 546/233; 548/578; 560/12; 562/826; 564/440
[58] Field of Search ............ 562/826; 514/576; 564/440

[56] References Cited

FOREIGN PATENT DOCUMENTS 1104968 1/1958 Fed. Rep. of Germany.
2557523 7/1976 Fed. Rep. of Germany.
2050409 1/1981 United Kingdom.

OTHER PUBLICATIONS

Krutak et al. "Chemistry of Ethanesulfonyl Fluoride," etc. J. Org. Chem. vol. 44(22) (1979) pp. 3847-3858.

Primary Examiner—Glennon H. Hollrah
Assistant Examiner—P. O'Sullivan
Attorney, Agent, or Firm—Benjamin F. Lambert

[57] ABSTRACT

The synthesis of novel ethanesulfonamide compounds is described. The novel ethanesulfonamide compounds have antisecretory activity and are used in the treatment of peptic ulcer disease. The intermediates used to prepare the ethanesulfonamides are useful in the treatment of osteoporosis and other bone wasting diseases.

7 Claims, No Drawings

ETHANESULFONAMIDE DERIVATIVES

This is a continuation-in-part of application Ser. No. 240,976 filed Sep. 6, 1988.

BACKGROUND OF THE INVENTION

The present invention relates to novel ethanesulfonamide derivatives in which the sulfonamide moiety is bonded to a 3-(cycloalkylaminomethyl)phenoxyalkylamine. The ethanesulfonamide derivatives are useful as antisecretory agents which can be used in the treatment of peptic ulcer disease.

SUMMARY OF THE INVENTION

The present invention is directed to ethanesulfonamide compounds of the formula

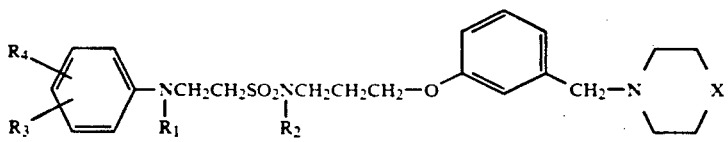

where
$R_1$ may be hydrogen or $C_1$-$C_3$ alkyl;
$R_2$ may be hydrogen or a pharmaceutically acceptable alkali or alkaline earth metal ion such as sodium, potassium, calcium or magnesium;
$R_3$ may be hydrogen, Cl, Br, F, $C_1$-$C_6$ alkyl, $C_3$-$C_6$ branched-chain alkyl, $C_1$-$C_6$ alkoxy, $C_3$-$C_6$ branched-chain alkoxy, $CF_3$, nitro, —NHCO$C_1$-$C_3$ alkyl, $NR_5R_6$ or $CO_2R_7$ when $R_4$ is hydrogen, or $R_3$ and $R_4$ are the same or different and are Cl, Br, F or $CF_3$;
$R_5$ and $R_6$ are the same or different and may be hydrogen or $C_1$-$C_3$ alkyl;
$R_7$ may be hydrogen or $C_1$-$C_6$ alkyl;
X may be O, $NR_8$, $CHR_8$ or —$(CH_2)_n$—;
$R_8$ may be $C_1$-$C_3$ alkyl; and
n may be 0, 1, 2, or 3; and its physiologically acceptable salts.

The ethanesulfonamide derivatives are useful as antisecretory agents which can be used in the treatment of peptic ulcer disease.

No examples of a sulfonamide moiety bonded to a 3-(cycloalkylaminomethyl)phenoxyalkylamine have been found in the literature.

DETAILED DESCRIPTION OF THE INVENTION

The invention in its broadest aspects relates to ethanesulfonamide derivatives which have antisecretory activity in mammals. The ethanesulfonamide compounds of the invention demonstrating antisecretory activity are shown in the above formula.

The preferred compounds of the present invention are those wherein $R_1$ and $R_2$ are hydrogen; $R_3$ is hydrogen, Cl, Br, F, nitro, $C_1$-$C_6$ alkyl, $C_3$-$C_6$ branched-chain alkyl, $CF_3$ or $CO_2R_7$, and $R_4$ is hydrogen, or $R_3$ and $R_4$ are each Cl or $CF_3$; $R_7$ is $C_1$-$C_6$ alkyl;
X is —$(CH_2)_n$—; and
n is 1 or 2.

The ethanesulfonamide derivatives of the present invention are prepared as shown in Scheme I.

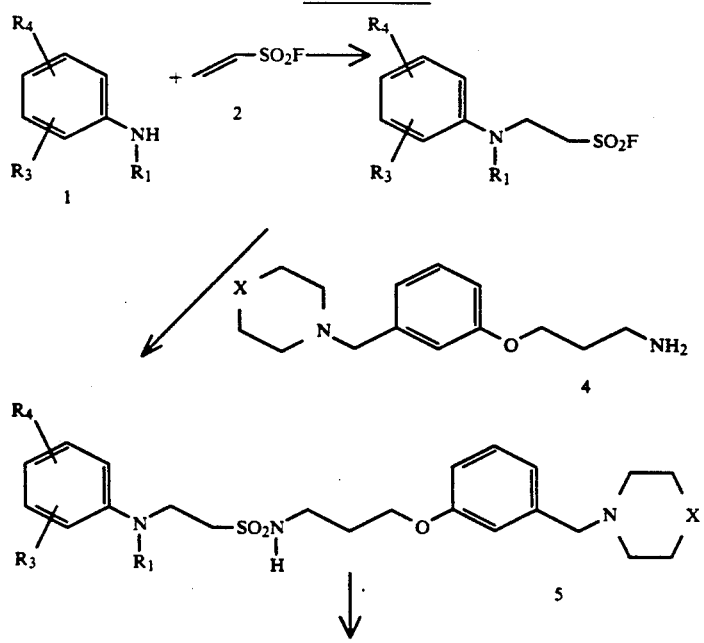

SCHEME I

SCHEME I

-continued

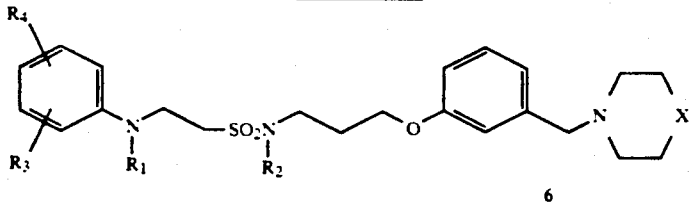

6

The ethanesulfonamide derivatives of the present invention are prepared as follows:

The aniline 1 is obtained as a commercial material or where $R_1$ is lower alkyl, the aniline is prepared by literature procedures such as G.W. Gribble et al., *J.Am. Chem.Soc.* 96, 7812 (1974). The ethenesulfonyl fluoride 2 is obtained as a commercial material or Prepared by the literature procedure of J.J. Krutak et al., *J. Org. Chem.* 44, 3847 (1979). The aniline 1 wherein $R_3$ and $R_4$ may represent hydrogen, 4-bromo, 4-fluoro, 3,4-dichloro, 4-butyl, 4-pentoxy, 4-isopropoxy, 4-chloro-3-trifluoromethyl, 4-nitro, 4-acetylamino, 4-ethoxycarbonyl, or 4-methylmercapto or other substituents, is mixed with ethenesulfonyl fluoride in an inert solvent such as toluene, acetic acid, dioxane, or N,N-dimethylformamide at a temperature of about 100°-130° C. for about three to 72 hours to afford the ethanesulfonyl fluoride 3.

The crude sulfonyl fluoride 3 is reacted with the phenoxypropylamines 4, which are known compounds described in the literature, wherein X may be O or NR (Merck and Co. European Patent 40696), wherein $R_7$ is lower alkyl, or X may be $CHR_7$ or $—(CH_2)_n—$, wherein n may be 0, 1, 2 or 3 (Bristol-Meyers Co., French Patent 2505835). The reaction may be done without a solvent or in an inert basic solvent such as triethylamine, pyridine, lutidine, quinoline or 1,8-diazabicyclo[5.4.0]undec-7-ene at about 80° C. to about 120° C. for about 18 to 20 hours. The sulfonamide 5 is obtained as a viscous liquid which may be mixed with a pharmaceutically acceptable acid such as, for example, ethanedioic acid, (E)- or (Z)-2-butenedioic acid, butanedioic acid, or HCl, or other acids, in an inert solvent such as methanol, ethanol, isopropanol, acetone or ether to afford an acid salt of sulfonamide 5 as a solid. The free-base sulfonamide 5 may also be mixed with a base such as, for example, NaOH, KOH, or $Ca(OH)_2$, or other bases, in an inert solvent such as methanol, ethanol or isopropanol to afford sulfonamide 5 after solvent removal as a solid, wherein $R_2$ is a pharmaceutically acceptable alkali or alkaline earth metal ion. The free-base sulfonamide 5, wherein $R_3$ is $NHCOCH_3$, may be treated with one equivalent of NaOH or KOH in an inert solvent such as methanol or ethanol to Produce the sulfonamide 5, wherein $R_3$ is $NH_2$.

Pharmaceutical compositions containing a compound of the present invention as the active ingredient in intimate admixture with a pharmaceutical carrier can be prepared according to conventional pharmaceutical compounding techniques The carrier may take a wide variety of forms depending on the form of preparation desired for administration, e.g., intravenous, oral, parenteral, aerosol or topical. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions elixirs and solutions) or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included Injectable suspensions may also be prepared, in which case appropriate liquid carriers, suspending agents and the like may be employed The pharmaceutical compositions will generally contain per dosage unit, e.g., tablet, capsule, powder, injection, teaspoonful and the like, from about 100 to about 2400 mg/kg, and preferably from about 250 to about 800 mg/kg of the active ingredient.

The substituted ethanesulfonyl fluoride compounds which are employed as intermediates in the Preparation of the ethanesulfonamide derivatives are also active compounds. The ethanesulfonyl fluoride intermediates are capable of increasing bone formation and bone mass and as such are useful in the treatment of osteoporosis and related bone-wasting diseases.

Osteoporosis is a common disabling bone disease which results in the gradual loss of bone mass per unit volume which makes it weak and porous and leads to increased incidence of spine, hip and forearm fractures ["Osteoporosis: Etiology, Diagnosis, and Management", B. Lawrence Riggs and L. Joseph Melton Eds, 1988]. Unfortunately, current medical treatments are only effective in preventing further bone loss (e.g. estrogen replacement, bisphosponates, vitamin D metabolites and calcium supplements). Once the osteoporotic disease has developed, the loss in bone mass causes an increase in fractures, which the above preventative treatments are of limited value. An ideal goal of therapy in patients with established bone loss is to provide a treatment program that will increase bone mass, i.e. restore lost bone and thus decrease the incidence of fractures and back/joint pain. Wit the exception of sodium fluoride; however, most available treatments fail to increase bone mass.

Sodium fluoride has been shown to be one agent that increases bone formation and leads to an increase in bone mass in osteoporosis. It is known that fluoride causes proliferation and increases the activity of bone forming cells, osteoblasts (Farley, et al., Science, 1983, 222, 330). Fluoride, together with adequate calcium supplementation, stimulates formation of mineralized bone. Moreover, the rate of bone fracture has been shown to be significantly decreased by fluoride treatment (Riggs, et al., N. Engl. J. Med., 1982, 306, 446).

Unfortunately, sodium fluoride has been associated with adverse reactions which include gastrointestinal side effects (nausea, vomiting, diarrhea and bleeding) and rheumatic complications (synovitis and plantar fascial syndrome). The frequency of these complications has decreased the widespread acceptance of sodium fluoride for the treatment of osteoporosis. Thus, the ideal treatment of bone los associated with osteoporosis and related bone-wasting diseases should embody an agent which possesses the "bone mitogen" activity of fluoride but lacks its adverse side-effects.

The intermediates which have been found to demonstrate this utility are ethanesulfonyl fluorides of the formulas

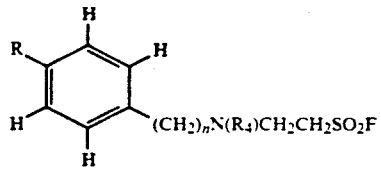

I

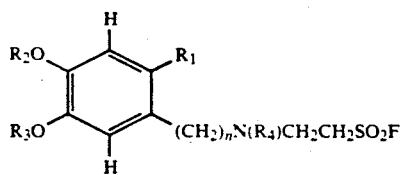

II where
R may be H, $C_1$-$C_5$ alkyl, $C_3$-$C_6$ branched-chain alkyl, $C_3$-$C_7$ cycloalkyl, $C_1$-$C_4$ alkoxy, Cl, F $CF_3$, $COR_5$, $CO_2R_5$, $CONHR_5$, or $NR_6R_7$;
$R_1$ may be H, $C_1$-$C_3$ alkyl, $COR_5$, $CO_2R_5$, $CONHR_5$, CN, or $S(O)_mCH_2R_5$;
$R_2$ and $R_3$ may be the same or different and may be H, $C_1$-$C_3$ alkyl, or $R_2$ and $R_3$ may be connected to form a 5-, 6- or 7-membered ring containing a methylenedioxy, ethylenedioxy or propylenedioxy group;
$R_4$ may be H, $C_1$-$C_5$ alkyl, $COR_8$, $CO_2R_8$ or $CONHR_8$;
$R_5$ may be H or $C_1$-$C_5$ alkyl;
$R_6$ and $R_7$ may be the same or different and may be $C_1$-$C_5$ alkyl;
$R_8$ may be H, $C_1$-$C_5$ alkyl, phenyl or substituted phenyl wherein the substituent is lower alkyl, lower alkoxy, halo, nitro or $CF_3$;
n may be 0-4;
m may be 0, 1 or 2;
with the provisos that
when n is zero then $R_2$ is not H;
when n is greater than zero then $R_4$ is not H;
and the Pharmaceutically acceptable acid addition salts thereof.

The compounds of formulas I and II are useful as cell growth stimulators and in particular as bone mitogens which can be used to treat patients with osteoporosis.

Certain ethanesulfonyl fluorides have been reported in the literature. Compounds of the formula

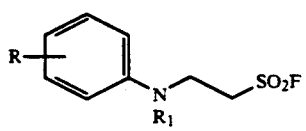

have been reported in by J. A. Hyatt and J. J. Krutak, J. Org. Chem., (1977), 42, 169; J. J. Krutak, R. D. Brupitt, W. H. Moore and J. A. Hyatt, J. Org. Chem; (1979), 44, 3847; and S. P. McManus, M. R. Smith, R. A. Abramovitch, and M. H. Offor, J. Org. Chem. (1984), 49, 683. Similar compounds have been reported in U.S. Pat. No. 4,265,812 and German Patent No. 1104968.

Compounds of the formula

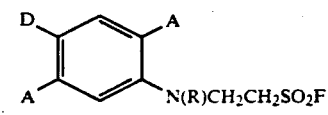

2 have been reported in German Patent No. 2557523.

None of the ethanesulfonyl fluoride derivatives reported in the literature have been shown to increase bone mass and bone formation. Some of the ethanesulfonyl fluorides having this utility are novel compounds and as such are part of the present invention. The novel ethanesulfonyl fluorides include:

2-[(2-Acetyl-4,5-dimethoxyphenyl)amino]ethanesulfonyl Fluoride;

2-[(4-Carboethoxyphenyl)amino]ethanesulfonyl Fluoride;

2-[(4-Methoxyphenyl)amino]ethanesulfonyl Fluoride Monohydrochloride;

2-[(4-Butylphenyl)amino]ethanesulfonyl Fluoride Monohydrochloride;

2-[(4-Fluorophenyl)amino]ethanesulfonyl Fluoride Monohydrochloride;

2-[(4-Methylphenyl)amino]ethanesulfonyl Fluoride;

2-[(3,4-Dimethoxyphenyl)amino]ethanesulfonyl Fluoride Monohydrochloride;

2-[(4-Trifluoromethylphenyl)amino]ethanesulfonyl Fluoride;

N-[2-(Fluorosulfonyl)ethyl]-3,4-dimethoxy-n-methylphenethylamine;

2-[(4-Ethylphenyl)amino]ethanesulfonyl Fluoride Monohydrochloride;

2-[(4-tert-Butylphenyl)amino]ethanesulfonyl Fluoride ¼ Hydrate;

2-[(4-Isopropylphenyl)amino]ethanesulfonyl Fluoride ¼ Hydrate.

The compounds of formula I are prepared as follows:

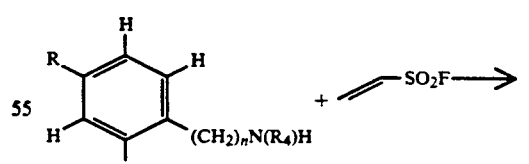

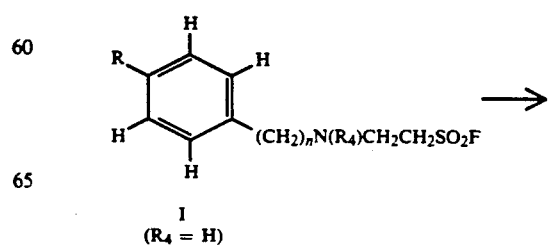

I
($R_4$ = H)

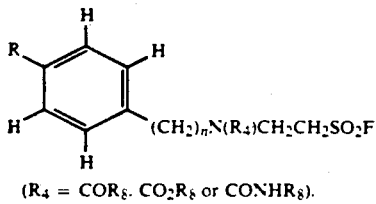

(R₄ = COR₈, CO₂R₈ or CONHR₈).

The 4-substituted phenyl alkylamines or 4-substituted anilines (n=0) were obtained from commercial sources or, where R₄ is lower alkyl, the compounds were prepared by standard literature procedures such as that of G. W. Gribble, et. al , J Amer. Chem. Soc., 1974, 96, 7812. The ethenesulfonyl fluoride was also obtained from a commercial source. The amine or aniline used as the starting material is mixed with ethenesulfonyl fluoride in an inert solvent such as toluene, acetic acid, dioxane, or N,N-dimethylformamide at room temperature or about 100°–130° C. depending upon the solvent employed, for 1 to 24 hours to afford the ethanesulfonyl fluoride I. The fluoride compound is then further reacted with an acid halide such as acetyl chloride, propionyl chloride, trimethylacetyl chloride, benzoyl chloride, 4-chlorobenzoyl chloride, or 4-methoxybenzoyl chloride, among others, in an inert solvent such as methylene chloride, dioxane, or tetrahydrofuran in the presence of a base such as pyridine, triethylamine, sodium bicarbonate, 4-dimethylaminopyridine, or DBU among others at room temperature. Compounds I (R₄=H) may also be reacted with various acid anhydrides such as acetic anhydride, propionic anhydride, trimethylacetic anhydride among others in an inert solvent such as methylene chloride, tetrahydrofuran or dioxane at room temperature or refluxing solvent temperature. The acid halide or acid anhydride reactions produce I where R₄ is COR₈. The ethenesulfonyl fluorides I (R₄=H) may be reacted with a halocarbonate such as methyl chloroformate, ethyl chloroformate, butyl chloroformate, or phenyl chloroformate among others in an inert solvent such as methylene chloride, dioxane, or tetrahydrofuran in the presence of a base such as pyridine, triethylamine, sodium bicarbonate, 4-dimethylaminopyridine, or DBU among others at room temperature to afford I where R₄ is CO₂R₈. Compounds I (R₄=H) may also be reacted with isocyanates such as methyl isocyanate, ethyl isocyanate, butyl isocyanate, tert-butyl isocyanate, phenyl isocyanate, 4-chlorophenyl isocyanate, or 4-methoxyphenyl isocyanate among others in an inert solvent such as methylene chloride, toluene, dioxane, or tetrahydrofuran at room temperature or refluxing solvent temperature to produce the ethenesulfonyl fluorides I where R₄ is CONHR₈.

The compounds of formula II are prepared as follows:

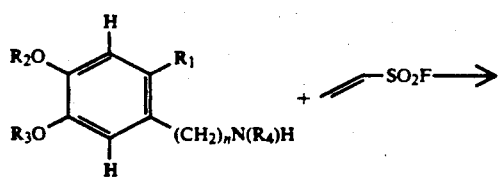

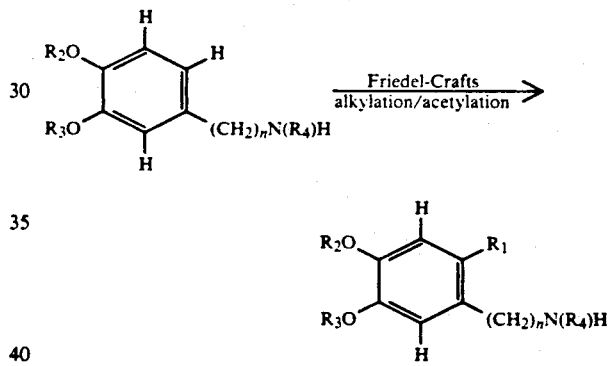

(R₄ = COR₈, CO₂R₈ or CONHR₈)

The 2,4,5-trisubstituted-phenyl alkylamines or 2,4,5-trisubstituted anilines (n=0) were obtained from commercial sources or by standard Friedel-Crafts alkylation/acetylation chemistry for the addition of R₁ substituent, i.e.

Where R₄ is lower alkyl, the compounds were prepared by the above mentioned Procedure. The amines or anilines wherein R₁ may represent hydrogen, methyl, ethyl, propyl, acetyl, propionyl, methoxycarbonyl, ethoxycarbonyl, aminocarbonyl, methylaminocarbonyl, propylaminocarbonyl, cyano, methylmercapto, methylsulfinyl, methylsulfonyl, ethylsulfinyl or ethylsulfonyl or other substitutents while R₂ and R₃ are methyl, or ethyl or when R₃ is hydrogen, R₂ is methyl or ethyl; and finally R₂ and R₃ may be joined to form a 5-, 6-, or 7-membered ring such as

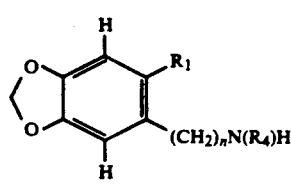

and

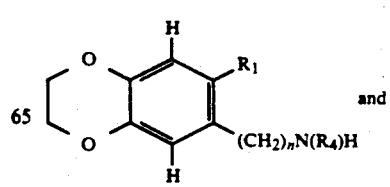

-continued

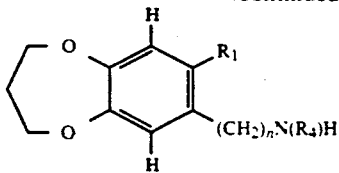

The starting material is mixed with ethenesulfonyl fluoride as described above. These ethenesulfonyl fluorides II ($R_4 = H$) can be reacted as mentioned above to produce II where $R_4$ is $COR_8$ or $CO_2R_8$ or $CONHR_8$.

Pharmaceutical compositions containing an ethenesulfonyl fluoride of the present invention as the active ingredient in intimate admixture with a Pharmaceutical carrier can be prepared according to conventional pharmaceutical compounding techniques. The pharmaceutical compositions will generally contain per dosage unit, e.g., tablet, capsule, Powder, injection, teaspoonful and the like, from about 0.1 to about 500 mg/kg of the active ingredient.

The following examples describe the invention in greater particularity and are intended to be a way of illustrating but not limiting the invention.

EXAMPLE 1

2-[(3,4-Dichlorophenyl)amino]-N-[3-[3-piperidinomethyl)phenoxy]propyl]ethanesulfonamide A N,N-dimethylformamide solution (DMF, 100ml) of 3,4-dichloroaniline (6.48 g, 40 mmol) and ethenesulfonyl fluoride (6.7 g, 57.9 mmol) was warmed to 110° C. for three hours. The cooled dark solution was diluted to 400 ml with water and the resulting dark oily precipate was decanted from the supernatant layer. This layer was extracted with ether (4×50 ml). The combined ether extracts were added to the oily precipitate and this dark solution was washed with brine and dried over $MgSO_4$. The organic solution was evaporated to give the crude 2-[(3,4-dichlorophenyl)amino]ethenesulfonyl fluoride as a dark liquid in quantitative yield.

The above Product (2.54 g, 9.33 mmol) was mixed with 3-[3-(piperidinomethyl)phenoxy]propylamine (2.6 g, 10.5 mmol) in 10 ml of pyridine. After the solution had been warmed to 100° C. for 18 hours under nitrogen, it was cooled and diluted to 100 ml with $H_2O$. A dark oily precipitate was isolated and dissolved in $CH_2Cl_2$, washed with $H_2O$ and brine and dried over $MgSO_4$. The organic solution was evaporated and the crude product was purified by flash silica gel (220 g) chromatography using 50% EtOAc in hexane and then EtOAc to afford the title compound (1.6 g, 34.3% Yield) as a yellow viscous liquid. This material was converted to its monooxalate salt in acetone, mp 112°-120° C.

Theor. $C_{23}H_{31}Cl_2N_3O_3S \cdot C_2H_2O_4$: C, 50.85; H, 5.63; N, 7.12;

Found: C, 50.83; H, 5.63; N, 6.97;

When in the above procedure, 4-nitroaniline, aniline or N-ethylaniline is used in place of the dichloroaniline, the corresponding (4-nitrophenyl)amino, phenylamino or N-ethylphenylamino derivative is obtained.

EXAMPLE 2

2-[(4-Fluorophenyl)amino]-N-[3-[3-(piperidinomethyl)phenoxy]propyl]ethanesulfonamide The 2-[(4-fluorophenyl)amino]ethenesulfonyl fluoride was produced following the procedure of Example 1 using 4-fluoroaniline (3.33 g, 30 mmol) and ethenesulfonyl fluoride (3.63 g, 33 mmol).

The title compound was produced following the procedure of Example 1 using the above crude ethenesulfonyl fluoride (6.65 g, 30 mmol) and the amine (8.18 g, 33 mmol) in Example 1. The title compound was isolated as a light yellow-green oil in 21.7% yield (2.93 g) after silica gel (200 g) chromatography and was converted to its monooxalate salt in acetone (softens at 115° C., mp 122°-124° C.).

Theor. $C_{23}H_{32}FN_3O_3S \cdot C_2H_2O_4$: C, 55.65; H, 6.,35 N, 7.79;

Found: C, 55.50; H, 6.61; N, 7.95;

EXAMPLE 3

2-[(4-Ethoxycarbonylphenyl)amino]-N-[3-[3-piperidinomethyl)phenoxy]propyl]ethanesulfonamide The crude 2-[(4-ethoxycarbonylphenyl)amino]ethane sulfonyl fluoride was produced following the procedure of Example 1 using ethyl 4-aminobenzoate (4.96 g, 30 mmol) and ethenesulfonyl fluoride (30 mmol) at 120° C. for 24 hours.

The title compound was produced following the procedure of Example 1 using the above ethenesulfonyl fluoride (6.55 g, 23.8 mmol) and the amine (6.49 g, 26.2 mmol) in Example 1. The title compound was purified by silica gel (200 g) chromatography and converted to its monooxalate salt in acetone in 21.3% yield (3.01 g) (softens at 126°-134° C., mp >250° C.)

Theor. $C_{26}H_{37}N_3O_5S \cdot C_2H_2O_4$: C, 56.65; H, 6.62; N, 7.08;

Found: C, 56 55; H, 6.81; N, 7 19;

EXAMPLE 4

2-[(4-Nitrophenyl)amino]-N-[3-[3-(piperidinomethyl)phenoxy]propyl]ethanesulfonamide The crude 2-[(4-nitrophenyl)amino]ethenesulfonyl fluoride was produced following the procedure of Example 1 using 4-nitroaniline (6.91 g, 50 mmol) and ethenesulfonyl fluoride (6.06 g, 66 mmol) at 110° C. for three days.

The title compound was produced following the procedure of Example 1 using the above ethenesulfonyl fluoride (9.88 g, 39.5 mmol) and the amine (10.77 g, 43.4 mmol) in Example 1. The title compound was isolated as an orange-yellow oil in 20% yield (3.80 g) after silica gel (200 g) chromatography and was converted to its monooxalate salt in acetone, mp 140°-142° C.

Theor. $C_{23}H_{32}N_4O_5S \cdot C_2H_2O_4$: C, 52.99; H, 6.05; N, 9.89;

Found: C, 52.57; H, 6.16; N, 9.85;

EXAMPLE 5

2-[(4-Bromophenyl)amino]-N-[3-[3-piperidinomethyl)phenoxy]propyl]ethanesulfonamide The crude 2-[(4-bromophenyl)amino]ethenesulfonyl fluoride was produced following the procedure of Example 1 using 4-bromoaniline (5.16 g, 30 mmol) and ethenesulfonyl fluoride (33 mmol).

The title compound was produced following the procedure of Example 1 using the above ethenesulfonyl fluoride (8.51 g, 30 mmol) and the amine (8.18 g, 33 mmol) in Example 1 The title compound was Purified by flash silica gel (200 g) chromatography and the resulting golden-brown oil was converted to its monooxalate salt in acetone in 5.6% yield (1.0 g), mp 119°–121° C.

Theor. $C_{23}H_{32}BrN_3O_3S.C_2H_2O_4$: C, 49.99; H, 5.71; N, 7.00;

Found: C, 50.05; H, 5.80; N, 7.07;

EXAMPLE 6

2-(Phenylamino)-N-[3-[3-(piperidinomethyl)phenoxy]-propyl]ethanesulfonamide

The crude 2-(phenylamino)ethenesulfonyl fluoride was Produced following the procedure of Example 1 using aniline (2.79 g, 30 mmol) and ethenesulfonyl fluoride (33 mmol).

The title compound was produced following the procedure of Example 1 using the above ethenesulfonyl fluoride (5.76 g, 28.3 mmol) and the amine (7.73 g, 31.2 mmol) in Example 1. The title compound was isolated in 13% yield (1.7 g) after flash silica gel (200 g) chromatography using $CH_2Cl_2/MeOH/NH_4OH$ (96/3.5/0.5), and the resulting yellow gum was converted to its monooxalate salt in acetone, mp 111.5°–115° C.

For $C_{23}H_{33}N_3O_3S.C_2H_2O_4.\frac{1}{2}H_2O$:
Theor.: C, 56.58; H, 6.84; N, 7.92;
Found: C, 56.73; H, 6.88; N, 7.60;

EXAMPLE 7

2-[[4-(1-Methylethoxy)Phenyl]amino]-N-[3-[3-(piperidinomethyl)Phenoxy]propyl]ethanesulfonamide The crude 2-[[4-(1-methylethoxy)phenyl]amino]ethenesulfonyl fluoride was produced following the procedure of Example 1 using 4-(1-methylethoxy)aniline (7.30 g, 48 mmol) and ethenesulfonyl fluoride (53 mmol).

The title compound was produced following the procedure of Example 1 using the above ethenesulfonyl fluoride (7.86 g, 30 mmol) and the amine (8.18 g, 33 mmol) in Example 1. The title compound was isolated in 7.2% yield (1.7 g) after flash silica gel (200 g) chromatography using $CH_2Cl_2/MeOH/NH_4OH$ (96/3.5/0.5) and was converted to its monooxalate salt in acetone, mp 110°–122° C.

For $C_{26}H_{39}N_3O_4S.C_2H_2O_4.\frac{1}{2}H_2O$:
Theor.: C, 57.12; H, 7.19; N, 7.14;
Found: C, 57.04; H, 7.13; N, 6.90;

EXAMPLE 8

2-[(4-Pentoxyphenyl)amino]-N-[3-[3-(piperidinomethyl)phenoxy]propyl]ethanesulfonamide The crude 2-[(4-pentoxyphenyl)amino]ethenesulfonyl fluoride was produced following the procedure of Example 1 using 4-Pentoxyaniline (10.4 g, 58.1 mmol) and ethenesulfonyl fluoride (60 mmol).

The title compound was produced following the procedure of Example 1 using the above ethenesulfonyl fluoride (10.71 g, 37 mmol) and the amine (10.0 g, 40.7 mmol) in Example 1. The title compound was isolated in 12% yield (3.5 g) after flash silica gel (200 g) chromatography using $CH_2Cl_2/MeOH/NH_4OH$ (97/2.5/0.5) and was converted to its dioxalate salt in methanol, mp 156.5°–160° C. (dec).

Theor. $C_{28}H_{43}N_3O_4S.2(C_2H_2O_4)$: C, 55.08; H, 6.79; N, 6.02;

Found: C, 55.18; H, 6.89; N, 6.28;

When in the above Procedure, 4-methoxyaniline or 4-butoxyaniline is used in place of the 4-pentoxyaniline, the corresponding (4-methoxyphenyl)amino or (4-butoxyphenyl)amino derivative is obtained.

EXAMPLE 9

2-[(4-Chloro-3-trifluoromethylphenyl)amino]-N-[3-[3-(piperidinomethyl)phenoxy]propyl]ethanesulfonamide The crude 2-[(4-chloro-3-trifluoromethylphenyl)amino]ethenesulfonyl fluoride was produced following the Procedure of Example 1 using 5-amino-2-chlorobenzotrifluoride (4.9 g, 25 mmol) and ethenesulfonyl fluoride (27.5 mmol).

The title compound was produced following the procedure of Example 1 using the above ethenesulfonyl fluoride (7.7 g, 25 mmol) and the amine (7.4 g, 30 mmol) in Example 1. The title compound was isolated in 15% Yield (2.0 g) as a yellow gum after flash silica gel (200 g) chromatography and was converted to its monooxalate salt in acetone. This tan solid was recrystallized from acetone/ether, mp 115°–120° C.

For $C_{24}H_{31}ClF_3N_3O_3S.C_2H_2O_4$:
Theor.: C, 50.04; H, 5.33; N, 6.73;
Found: C, 50.06; H, 5.29; N, 6.64;

EXAMPLE 10

2-[(4-Butylphenyl)amino]-N-[3-[3-(piperidinomethyl)-phenoxy]propyl]ethanesulfonamide The crude 2-[(4-butylphenyl)amino]ethenesulfonyl fluoride was produced following the procedure of Example 1 using 4-butylaniline (4.5 g, 30 mmol) and ethenesulfonyl fluoride (33 mmol).

The title compound was produced following the procedure of Example 1 using the above ethenesulfonyl fluoride (30 mmol) and the amine (8.1 g, 33 mmol) in Example 1. The title compound was isolated in 20% yield (3.0 g) as a Yellow oil after flash silica gel (200 g) chromatography using $CH_2Cl_2/EtOH/NH_4OH$ (96/3.5/0.5) and was converted to its dioxalate salt in MeOH/acetone/ ether, mp 115°–119° C.

For $C_{27}H_{41}N_3O_3S.2(C_2H_2O_4)$:
Theor.: C, 55,76; H, 6.79; N, 6.29;
Found: C, 55.89; H, 6.80; N, 6.35;

When in the above Procedure, 4-ethylaniline or 4-isopropylaniline is used in place of the 4-butylaniline, the corresponding (4 ethylphenyl)amino or (4-isopropylphenyl)amino derivative is obtained.

EXAMPLE 11

2-[(3,4-Dichlorophenyl)amino]-N-[3-[3-[(4-methylpiperidin-1-yl)methyl]-phenoxy]propyl]ethanesulfonamide The title compound was produced following the procedure of Example 1 using the ethenesulfonyl fluoride (3.4 g, 12.5 mmol) of Example 1 and 3-[3-[(4-methylpiperidin-1-yl)methyl]phenoxy]propylamine (3.4 g, 12.9 mmol) at reflux for 20 hours. The title compound was isolated in 66.9% yield (4.3 g) as an orange liquid and was converted to its monooxalate salt in acetone/ether, mp 130°–135° C.

For $C_{24}H_{33}Cl_2N_3O_3S.C_2H_2O_4$:
Theor.: C, 51.65; H, 5.84; N, 6.95;
Found: C, 51.78; H, 5.90; N, 6.84;

When in the above procedure, 3-[3-(pyrrolidinomethyl)Phenoxy]propylamine or 3-[3-(piperazinomethyl)-Phenoxy]Propylamine is used, the corresponding 3-[3-(pyrrolidinomethyl)phenoxy]propyl or 3-[3-

(piperazinomethyl)phenoxy]propyl derivative is obtained.

EXAMPLE 12

Pharmacology of the Ethanesulfonamide Compounds - Rabbit Isolated Parietal Cells Parietal cells were isolated from the fundic mucosa of rabbit stomachs by a four-stage collagenase digestion Process. The supernatant fraction from the last two stages of this Process contained the individual parietal cells. This cell suspension was centrifuged and reconstituted in a modified Hank's buffer to contain $2-3 \times 10^6$ cells/ml. The cells in this suspension were then evaluated for their ability to accumulate $^{14}$C-aminopyrine ($^{14}$C-AP), a weak base which has been shown to accumulate in acidic environments such as the parietal cell. The accumulation is stimulated by histamine and is blocked by $H_2$ antagonists. Accumulation of $^{14}$C-AP is also stimulated by dibutyryl cAMP (dbcAMP). The cells were incubated with $0.5 \times 10^6$ cpm $^{14}$C-AP, with various concentrations of histamine or dbcAMP, $1 \times 10^5$ M isobutylmethylxanthine, and test compound added in a 20 μl volume of buffer or dimethylsulfoxide. The flasks were incubated in a shaking water bath at 37° C. Two 0.5 ml aliquots were then taken from each flask and cell pellets were collected by centrifugation. The pellets were solubilized with Protosol (NEN) and radioactivity determined by liquid scintillation spectrometry.

The concentration of compound required to inhibit $^{14}$C-AP accumulation in the stimulated parietal cell by 50% ($IC_{50}$) was determined. Table 1 shows the $IC_{50}$s of the compound of Examples 1-11 above.

TABLE 1

| Example (Compound) | $IC_{50}$ Data Against Histamine (H) and dbcAMP | |
|---|---|---|
| | $IC_{50}$(H) (μM) | $IC_{50}$(dbcAMP) (μM) |
| 1 | 0.37 | 0.13 |
| 2 | 0.92 | 1.82 |
| 3 | 0.39 | 2.30 |
| 4 | 0.12 | 3.70 |
| 5 | 0.37 | 0.86 |
| 6 | 1.0 | 10.0 |
| 7 | 0.84 | 2.0 |
| 8 | 0.33 | 0.37 |
| 9 | 0.16 | 0.31 |
| 10 | 0.28 | 0.23 |
| 11 | 0.058 | 0.46 |

EXAMPLE 13

Inhibition of Gastric Secretion in Rat

Male Charles River rats weighing 150-300 grams were deprived of food but not water for 18-24 hours prior to use. Water was withheld during the experiment. The rats were weighed, anesthetized with ether and the pylorus ligated according to the method of Shay, H. et al., *Gastroenterol.* 26, 906 (1954). Test compounds were suspended in a 0.5% aqueous solution of methylcellulose (15 cps) and administered intraduodenally (i.d.) at the time of ligation. The rats were housed two per cage and sacrificed with $CO_2$ four hours after ligation. The stomachs were removed and contents emptied into a graduated centrifuge tube. The tubes were centrifuged, the volume of gastric juice recorded, and any samples obviously contaminated by feces, food or blood eliminated. A 1 ml aliquot of gastric juice was titrated with 0.1 N NaOH to a pH of 7.0-7.4.

The volume of gastric juice secreted, the acid concentration, and the product of the volume times the concentration, i.e., the total amount of acid secreted, were statistically compared by a student's t-test using the pooled error variance. The in vivo activity of these novel ethanesulfonamides is shown in Table 2.

TABLE 2

| Reduction of Gastric Secretion in Rat | | |
|---|---|---|
| Example (Compound) | % Reduction of Total Acid Output | Dose (MPK) |
| 1 | 47.9 | 40 |
| 2 | 22.1 | 40 |
| 3 | 25.6 | 40 |
| 4 | 30.8 | 40 |
| 9 | 24.7 | 40 |
| 10 | 23.3 | 20 |
| 11 | 29.0 | 20 |

EXAMPLE 14

2-[(2-Acetyl-4,5-dimethoxyphenyl)amino]ethenesulfonyl Fluoride

To a mixture of 2-amino-4,5-dimethoxyacetophenone (18 g, 92 mmol) in 125 mL of glacial acetic acid was added in one portion ethenesulfonyl fluoride (11.4 g, 0.1 mol) under nitrogen. After stirring for 1 hour at room temperature the resulting yellow mixture was refluxed for 1 hour. The yellow crystalline solid was diluted with an equal volume of ether, filtered, washed with ether, and air dried. There was obtained the title compound (23.7 g, 85% yield) as a yellow solid, mp 142.5°-146.5° C.

Theor. $C_{12}H_{16}FNO_5S$: C, 47.20; H, 5.28; N, 4.59;
Found: C, 47.18; H, 5.27; N, 4.49;

EXAMPLE 15

2-[(4-Chlorophenyl)amino]ethenesulfonyl Fluoride

To a DMF (50 mL) solution of 4-chloroaniline (3.0 g, 23.5 mmol) was added ethenesulfonyl fluoride (3.3 mL, 30 mmol). The solution was heated at 110° C. until the 4-chloroaniline was consumed (monitored by tlc). The orange solution was diluted with 1 liter of water and the resulting oily precipitate was extracted into ether. The combined organic layers was washed with water and brine and dried ($MgSO_4$). After the ether had been removed by distillation, the brown residue afforded the title compound (4.56 g, 81%) as yellow needles which could be crystallized from ether/hexane, mp 61°-63° C. (lit. mp 62°-63° C.; Hoechst's German Patent 1104968).

Theor. $C_8H_9ClFNO_2S$: C, 40.43; H, 3.82; N, 5.89;
Found: C, 40.70; H, 3.48; N, 5.79;

EXAMPLE 16

2-[(4-Carboethoxyphenyl)amino]ethenesulfonyl Fluoride

To a 75 mL DMF solution of 4-carboethoxyaniline (3.88 g, 23.5 mmol) was added ethenesulfonyl fluoride (3.3 mL, 30 mmol) under nitrogen. The solution was warmed to 100-120° C. for 6 hours. The cooled solution was slowly Poured into water and chilled in ice. The yellow solid precipitate was collected, dissolved in methylene chloride, washed with brine and dried ($Na_2SO_4$). After the solvent had been removed by distillation, the brown solid (5.4 g) was crystallized from methylene chloride/ether/hexane. The title compound (3.2 g, 49% yield) was obtained as a tan solid, mp 109.5°-111.5° C.

Theor. $C_{11}H_{14}FNO_4S$: C, 47.99; H, 5.13; N, 5.09;
Found: C, 47.98; H, 5.39; N, 4.94;

EXAMPLE 17

2-[(4-Methoxyphenyl)amino]ethenesulfonyl Fluoride Monohydrochloride

The reaction between 4-methoxyaniline (2.89 g, 23.5 mmol) and ethenesulfonyl fluoride (3.3 mL, 30 mmol) was carried out in DMF (75 mL) as described in Example 16. There was obtained a dark oily residue (4.0 g) which was dissolved in a minimal amount of IPA and treated with 1.1 equivalents of HCl/IPA. The title compound (4.12 g, 65% yield) was obtained as a beige solid, mp 157.5°-158° C. (dec).

Theor. $C_9H_{12}FNO_3S.NCl$: C, 40.08; H, 4.86; N, 5.19;
Found: C, 40.11; H, 4.66; N, 4.90;

EXAMPLE 18

2-(Phenylamino)ethenesulfonyl Fluoride Monohydrochloride

The reaction between aniline (2.19 g, 23.5 mmol) and ethenesulfonyl fluoride (3.3 mL, 30 mmol) was carried out in DMF (75 mL) as described in Example 16. There was obtained a light red oily residue (3.1 g) which was dissolved in a minimal amount of IPA and treated with 1.1 equivalents of HCl/IPA. The title compound (2.95 g, 52% yield) was obtained as a beige solid, mp 159.5°-161.5° C. [lit. bp 103°-105° C. (0.5 mm) for the free base; J. J. Krutak, et. al., J. Org. Chem., 1979, 44, 3847].

Theor. $C_8H_{10}FNO_2S.HCl$: C, 40.09; H, 4.63; N, 5.84;
Found: C, 40.14; H, 4.47; N, 5.60;

EXAMPLE 19

2-[(4-Butylphenyl)amino]ethenesulfonyl Fluoride Monohydrochloride

The reaction between 4-butylaniline (3.51 g, 23.5 mmol) and ethenesulfonyl fluoride (3.3 mL, 30 mmol) was carried out in DMF (75 mL) as described in Example 16. There was obtained a dark oily residue which was dissolved in a minimal amount of IPA and treated with 1.1 equivalents of HCl/IPA. The title compound (4.66 g, 67% yield) was obtained as a tan solid, mp 153°-156.5° C.

Theor. $C_{12}H_{18}FNO_2S.HCl$: C, 48.73; H, 6.47; N, 4.74;
Found: C, 48.70; H, 6.55; N, 4.55;

EXAMPLE 20

2-[(4-Fluorophenyl)amino]ethenesulfonyl Fluoride Monohydrochloride

The reaction between 4-fluoroaniline (2.61 g, 23.5 mmol) and ethenesulfonyl fluoride (3.3 mL, 30 mmol) was carried out in DMF (75 mL) as described in Example 16. There was obtained a dark oily residue (4.0 g) which was dissolved in a minimal amount of IPA and treated with 1.1 equivalents of HCl/IPA. The title compound (2.24 g, 37% Yield) was obtained as an off-white solid, mp 146°-147° C.

Theor. $C_8H_9F_2NO_2S.HCl$ C, 37.29; H, 3.91; N, 5.44; S, 12.44;
Found: C, 37.19; H, 3.81; N, 5.34; S, 12.74;

EXAMPLE 21

2-[(4-Methylphenyl)amino]ethenesulfonyl Fluoride

The reaction between 4-methylaniline (1.61 g, 15 mmol) and ethenesulfonyl fluoride (2.18 g, 19 mmol) was carried out in DMF (30 mL) at ambient temperature for 2.5 hours as described in Example 16. There was obtained a tan residue which was crystallized from ether/hexane to afford the title compound as a tan solid (1.12 g 34% yield), mp 61°-65° C.

Theor. $C_9H_{12}FNO_2S$: C, 49.76; H, 5.57; N, 6.45;
Found: C, 49.74; H, 5.70; N, 6.27;

EXAMPLE 22

2-[(3,4-Dimethoxyphenyl)amino]ethenesulfonyl Fluoride Monohydrochloride

The reaction between 3,4-dimethoxyaniline (2.30 g, 15 mmol) and ethenesulfonyl fluoride (2.18 g, 19 mmol) was carried out in DMF (30 mL) at ambient temperature for 2.5 hours as described in Example 16. There was obtained a dark brown oily material (3.90 g) which was dissolved in a minimal amount of IPA and treated with 1.0 equivalent of HCl/IPA. The title compound (3.99 g, 88% yield) was obtained as a silvery-purple solid, mp 195°-199° C.

Theor. $C_{10}H_{14}FNO_4S.HCl$ C, 40.07; H, 5.04; N, 4.67; S, 10.70;
Found: C, 40.14; H, 5.10; N, 4.52; S, 10.78;

EXAMPLE 23

2-[(4-Trifluoromethylphenyl)amino]ethenesulfonyl Fluoride

The reaction between 4-trifluoromethylaniline (2.42 g, 15 mmol) and ethenesulfonyl fluoride (1.65 mL, 19 mmol) was carried out in DMF (30 mL) at ambient temperature for 2 hours as described in Example 16. There was obtained on orange solid (3.53 g, 87%) which was crystallized from ether/hexane to afford the title compound as a pale Yellow solid (0.5 g, 12% yield), mp 71°-73° C.

Theor. $C_9H_9F_4NO_2S$: C, 39.85; H, 3.34; N, 5.16; S, 11.82;
Found: C, 39.96; H, 3.24; N, 4.91; S, 11.69;

EXAMPLE 24

N-[2-(Fluorosulfonyl)ethyl]-3,4-dimethoxy-N-methylphenethylamine

The reaction between 3,4-dimethoxy-N-methylphenethylamine (15 mmol) and ethenesulfonyl fluoride (1.65 mL, 19 mmol) was carried out in DMF (30 mL) at ambient temperature for 3 hours as described in Example 16. There was obtained an orange liquid which was crystallized from ether/methanol to afford the title compound as a yellow solid (0.14 g, 11% yield), mp 200°-204° C.

Theor. $C_{13}H_{20}FNO_4S$: C, 51.13; H, 6.60; N, 4.59;
Found: C, 50.88; H, 6.96; N, 4.36;

EXAMPLE 25

2-[(4-Ethylphenyl)amino]ethenesulfonyl Fluoride Monohydrochloride

The reaction between 4-ethylaniline (1.82 g, 15 mmol) and ethenesulfonyl fluoride (1.65 mL, 19 mmol) was carried out in DMF (30 mL) as described in Example 16. There was obtained a dark orange oily residue (3.19 g) which was dissolved in a minimal amount of IPA and treated with 1 equivalent of HCl/IPA. The title compound (2.39 g, 60% yield) was obtained as a gray-brown solid, mp 162°-164° C.

Theor. $C_{10}H_{14}FNO_2S.HCl$: C, 44.86; H, 5.65; N, 5.23;
Found: C, 44.59; H, 5.62; N, 4.98;

EXAMPLE 26

2-[(4-tert-Butylphenyl)amino]ethenesulfonyl Fluoride ¼ Hydrate

The reaction between 4-tert-butylaniline (2.24 g, 15 mmol) and ethenesulfonyl fluoride (1.65 mL, 19 mmol) was carried out in DMF (30 mL) as described in Example 16. There was obtained an orange oily residue (3.81 g) which crystallized upon standing. This material was recrystallized from methanol/water to produce 2.06 g (52% yield) of the title compound as a light pink solid, mp 67°-70.5° C. Theor. $C_{12}H_{18}FNO_2S.\frac{1}{4} H_2O$: C, 54.62; H, 7.07; N, 5.31;

Found: C, 54.35; H, 7.00; N, 5.15;

EXAMPLE 27

2-[(4-Isopropylphenyl)amino]ethenesulfonyl Fluoride ¼ Hydrate

The reaction between 4-isopropylaniline (2.03 g, 15 mmol) and ethenesulfonyl fluoride (1.65 mL, 19 mmol) was carried out in DMF (30 mL) as described in Example 16. There was obtained a brown oily residue (3.57 g) which crystallized upon standing. This material was recrystallized from methanol/water to produce 2.30 g (63% yield) of the title compound as a brown solid, mp 41°-43° C.

Theor. $C_{11}H_{16}FNO_2S.\frac{1}{4} H_2O$: C, 52.88; H, 6.66; N, 5.60;

Found: C, 52.89; H, 6.59; N, 5.40;

EXAMPLE 28

Pharmacology of the Ethenesulfonyl Fluoride Compounds—In Vitro Mouse Osteoblast-line Cell Proliferation Reagents: Mouse osteoblastic-line cells (MC3T3-El) were plated in Dulbeccos Modified Eagles Medium (DMEM) with 25 mM Hepes Buffer, L-Glutamine, D-Glucose(4.5 gm/l) supplemented with 10% fetal bovine sera, Penicillin (100 units/ml) and Streptomycin (100μl) (Penicillin-Streptomycin liquid) and sodium pyruvate (10 μM final concentration). $^3$H-Thymidine (6.7 Ci/mmole) was diluted in DMEM media without FBS and filter sterilized. An aliquot of this solution was delivered to each culture well to a final concentration of $^3$H-thymidine of 0.4 μCi per well (2 μCi/ml).

Test Preparations: Solutions of the test compound were made on the day before incubation. These compounds were solubilized in either ethanol or DMSO at a concentration of 100 mM containing 0.1% FBS. The solutions were filter sterilized and then sterile serial dilutions were performed with DMEM media containing 0.1% FBS.

Osteoblast line cells were plated into 96 well culture plates, 1600 cells in 100 μL per well in DMEM with 25 mM Hepes Buffer, L-Glutamine, D-Glucose (4.5 gm/L) supplemented with 10% fetal bovine sera, Penicillin (100 units/mL) and Streptomycin (100 μg/mL) and sodium Pyruvate (10 μM final concentration). The media was replaced with DMEM containing no FBS and the cells were then incubated for an additional 24 hours. The following day, test compounds were added and screened at concentrations ranging from $10^{-10}$ to $10^{-5}$ M in the Presence of 0.1% FBS. The cells were then incubated an additional 20 hours. At this time 0.4 μ/Ci of 3H-thymidine was added to each culture well and the cells were incubated an additional 4 hours. The cells were then harvested with a Skatron Cell Harvester onto a glass fiber filter and washed with water, %5 trichloroacetic acid (TCA) and then 95% ethanol. The filters were then processed and counted on the LKB beta plate scintillation counter. The results are shown below in Table 3.

EXAMPLE 29

Pharmacology of the Ethenesulfonyl Fluoride Compounds—In Vitro Bone Mitogen Activity in the Aged Fisher 344 Rat Animals: Female Fisher 344 rats, 12 months of age, were housed in climate controlled light/dark (12-hour cycle) rooms and given food and water ad libitum.

Test Compounds: The test compounds were suspended in sesame oil and administered daily via intraperitoneal injections; vehicle treated rats were administered sesame oil along (2 mL/kg).

In vivo [$^3$H]Proline Incorporation: [$^3$H]Proline incorporation into bone protein was carried out as previously described (Reddi and Huggins, 1975). [$^3$H]Proline was injected intraperitoneally at a dose of 0.5 μCi/g body weight in 0.9% NaCl. Four hours after the injection, rats were bled by cardiac puncture and then killed by $CO_2$ asphyxiation and the tibia removed and the radioactivity quantified as in Example 28. The results are shown below in Table 4.

In vivo [$^3$H]Tetracycline Incorporation: Tritiated tetracycline, which is rapidly concentrated in the growing skeleton, can be used as a relative measure of bone forming surface in vivo. [$^3$H]Tetracycline was injected intraperitoneally at a dose of 0.125 μCi/g body weight in a 0.9% NaCl solution. Two hours after injection, rats were bled by cardiac puncture and then killed by $CO_2$ asphyxiation and the tibia removed and cleaned of tissue and marrow. The tibia are homogenized and digested in 2 N NaOH for 2 hours. The precipitate is washed and then hydrolyzed in 6N Hcl. An aliquot of the resulting supernatant is analyzed for tritiutum. The results are shown below in Table 4.

TABLE 3

In Vivo Bone Mitogen Screening Summary
Mouse Osteoblast-line Cell Proliferation
[Expressed as a Percent of Control]

| Example # | Dose (μM) = 10 | 1.0 | 0.1 | 0.01 | 0.001 |
|---|---|---|---|---|---|
| 14 | 180.3 | 170.3 | 125.3 | 159.5 | 120.9 |
| 15 | 106.7 | 93.4 | 123.5 | 119.9 | 129.6 |
| 16 | 154.7 | 136.5 | 127.5 | 142.1 | 132.8 |
| 17 | 108.8 | 115.9 | 129.1 | 148.9 | 165.5 |
| 18 | 95.9 | 93.1 | 108.1 | 125.6 | 132.6 |
| 19 | 115.7 | 97.4 | 159.8 | 143.3 | 109.0 |
| 20 | 112.3 | 116.9 | 110.2 | 111.8 | 133.4 |
| 21 | 111.8 | 119.9 | 126.6 | 132.0 | 131.5 |
| 22 | 106.7 | 113.5 | 116.4 | 133.6 | 143.6 |
| 23 | 111.7 | 120.8 | 107.3 | 97.9 | 108.1 |
| 24 | 106.7 | 123.3 | 153.5 | 143.9 | 150.4 |
| 25 | 90.0 | 110.6 | 100.9 | 123.3 | 139.4 |
| 26 | 93.2 | 102.7 | 89.9 | 165.7 | 152.8 |
| 27 | 97.7 | 110.8 | 106.9 | 130.0 | 137.2 |

TABLE 4

In Vitro Bone Mitogen Screening Summary
[Expressed as a Percent Incorporation of [$^3$H] Tetracycline or [$^3$H]Proline of Control]

| Example # | Dose mg/Kg | [$^3$H]Tetracycline | [$^3$H]Proline |
|---|---|---|---|
| 14 | 15 | | 100.7 |
| | 50 | 119.6 | 118.1 |
| | 150 | | 121.0 |
| 15 | 15 | 118.0 | |
| | 25 | 114.0 | |

TABLE 4-continued

In Vitro Bone Mitogen Screening Summary
[Expressed as a Percent Incorporation of [³H] Tetracycline or [³H]Proline of Control]

| Example # | Dose mg/Kg | [³H]Tetracycline | [³H]Proline |
|---|---|---|---|
| | 50 | 125.1 | |

What is claimed is:

1. A compound of formula:

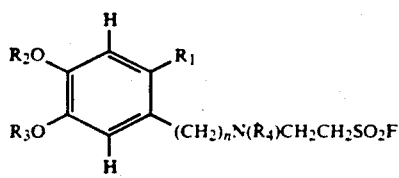

$R_1$ is $COR_5$;
$R_2$ and $R_3$ are $C_1$-$C_3$ alkyl;
$R_4$ is hydrogen of $C_1$-$C_5$ alkyl;
$R_5$ is hydrogen or $C_1$-$C_5$ alkyl; and
n is 0 or 2
provided that at least one of $R_2$, $R_3$ and $R_4$ is other than hydrogen.

2. A compound of claim 1 which compound is 2-[(2-Acetyl-4,5-dimethoxyphenyl)amino]ethane-sulfonyl Fluoride.

3. A method of increasing bone formation and bone mass in mammals which comprises administering to said mammal an effective amount of a compound of claim 1.

4. The method of claim 3 wherein the compound is 2-[(2-Acetyl-4,5-dimethoxyphenyl)amino]ethenesulfonyl Fluoride:

5. A method of treating osteoporosis in mammals which comprises administering to said mammal an effective amount of a compound of claim 1.

6. The method of claim 5 wherein the compound is 2-[(2-Acetyl-4,5-dimethoxyphenyl)amino]ethenesulfonyl Fluoride.

7. A pharmaceutical composition comprising an effective amount of a compound of claim 1 and a pharmaceutically acceptable carrier.

* * * * *